(12) United States Patent
Park et al.

(10) Patent No.: US 11,339,398 B2
(45) Date of Patent: *May 24, 2022

(54) ACID-RESISTANT YEAST WITH SUPPRESSED ETHANOL PRODUCTION PATHWAY AND METHOD FOR PRODUCING LACTIC ACID USING SAME

(71) Applicant: SK INNOVATION CO., LTD., Seoul (KR)

(72) Inventors: Jae Yeon Park, Daejeon (KR); Tae Young Lee, Daejeon (KR); Ki Sung Lee, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/047,810

(22) PCT Filed: Feb. 28, 2019

(86) PCT No.: PCT/KR2019/002433
§ 371 (c)(1),
(2) Date: Oct. 15, 2020

(87) PCT Pub. No.: WO2019/203436
PCT Pub. Date: Oct. 24, 2019

(65) Prior Publication Data
US 2021/0155945 A1 May 27, 2021

(30) Foreign Application Priority Data

Apr. 17, 2018 (KR) ........................ 10-2018-0044509

(51) Int. Cl.
| | | |
|---|---|---|
| C12N 9/02 | (2006.01) | |
| C12N 9/04 | (2006.01) | |
| C12P 7/20 | (2006.01) | |
| C12N 15/81 | (2006.01) | |
| C07K 14/39 | (2006.01) | |
| C12P 7/56 | (2006.01) | |

(52) U.S. Cl.
CPC .............. *C12N 15/81* (2013.01); *C07K 14/39* (2013.01); *C12N 9/0006* (2013.01); *C12P 7/56* (2013.01); *C12Y 101/01027* (2013.01)

(58) Field of Classification Search
CPC ......... C12N 15/81; C12N 9/0006; C12P 7/56; A23L 3/3463; C12Y 101/01027; C07K 14/39
USPC ................ 435/254.2, 161, 139, 252.2, 320.1
See application file for complete search history.

(56) References Cited

U.S. PATENT DOCUMENTS

| | | |
|---|---|---|
| 7,049,108 B2 | 5/2006 | Porro et al. |
| 7,141,410 B2 | 11/2006 | Rajgarhia |
| 7,534,597 B2 | 5/2009 | Hause et al. |
| 9,353,388 B2 | 5/2016 | Kim |

FOREIGN PATENT DOCUMENTS

| | | |
|---|---|---|
| JP | 2001204464 A | 7/2001 |
| JP | 4095889 B2 | 7/2004 |
| JP | 2005-137306 A | 6/2005 |
| JP | 4692173 B2 | 3/2007 |
| KR | 10-2016-0012561 A | 2/2016 |
| KR | 10-2016-0133308 A | 11/2016 |
| KR | 1686900 B1 | 12/2016 |
| KR | 10-2017-0025315 A | 3/2017 |
| KR | 102140596 B1 | 8/2020 |

OTHER PUBLICATIONS

Devos et al., Proteins: Structure, Function and Genetics, 2000, vol. 41: 98-107.*
Whisstock et al., Quarterly Reviews of Biophysics 2003, vol. 36 (3): 307-340.*
Witkowski et al., Biochemistry 38:11643-11650, 1999.*
Kisselev L., Structure, 2002, vol. 10: 8-9.*
International Search Report dated May 28, 2019 for corresponding PCT patent application No. PCT/KR2019/002433.
Garvie, Ellen I. "Bacterial lactate dehydrogenases." Microbiological reviews 44.1 (1980): 106.8-1070.
Sauer Michael et al. "16 years research on lactic acid production with yeast-ready for the market?." Biotechnology and Genetic Engineering Reviews 27.1 (2010): 229-256.
Zhang Yiming et al. "Adaptive mutations in sugar metabolism restore growth on glucose in a pyruvate decarboxylase negative yeast strain." Microbial cell factories 14.1 (2015): 116.
Ishida Nobuhiro et al. "Efficient production of L-lactic acid by metabolically engineered *Saccharomyces cerevisiae* with a genome-integrated L-lactate dehydrogenase gene." Applied and Environmental Microbiology 71.4 (2005): 1964-1970.
Savijoki Kirsi and Airi Palva "Molecular genetic characterization of the L-lactate dehydrogenase gene (IdhL) of Lactobacillus helveticus and biochemical characterization of the enzyme." Applied and environmental microbiology 63.7 (1997): 2850-2856.
Abbott, D.A., et al., Metabolic engineering of *Saccharomyces cerevisiae* for producti nof caboxylic acids: current status and challenges. FEMS Yeast Research 2009, vol. 9, pp. 1123-1136.
Feldmman-Salit Anna et al. "Regulation of the activity of lactate dehydrogenases from four lactic acid bacteria." Journal of Biological Chemistry 288.29 (2013): 21295-21306.

(Continued)

*Primary Examiner* — Robert B Mondesi
*Assistant Examiner* — Mohammad Y Meah
(74) *Attorney, Agent, or Firm* — Abelman, Frayne & Schwab; Stefan Knirr; Douglas Gilbert

(57) ABSTRACT

The present invention relates to an acid-resistant yeast endowed with a lactic acid production ability and having a suppressed ethanol production pathway, and a method for producing lactic acid using same. According to the present invention, by effectively suppressing the production of ethanol in an acid-resistant yeast, and by expressing an LDH enzyme with strong expression and high efficiency, it is possible to produce lactic acid with high yield even at low pH without degrading growth.

3 Claims, 5 Drawing Sheets

Specification includes a Sequence Listing.

(56) References Cited

OTHER PUBLICATIONS

Tokuhiro Kenro et al. "Double mutation of the PDC1 and ADH1 genes improves lactate production in the yeast *Saccharomyces cerevisiae* expressing the bovine lactate dehydrogenase gene." Applied microbiology and biotechnology 82.5 (2009): 883-890.
Christopher D. S. et al., Inhibition of Rhizopus lactate dehydrogenase by fructose 1,6-bisphosphate Enzyme and Microbial Technology 44(2009) 242-247, 2009.
Notice of Allowance dated Sep. 27, 2021 for corresponding KR patent application No. 10-2020-0093598.
Skory, Christopher D. "Lactic acid production by *Saccharomyces cerevisiae* expressing a Rhizopus oryzae actate dehydrogenase gene." Journal of Industrial Microbiology and Biotechnology 30.1 (2003): 22-27.

\* cited by examiner

```
                            SEQUENCE LISTING

<160> NUMBER OF SEQ ID NOS: 54

<210> SEQ ID NO 1
<211> LENGTH: 320
<212> TYPE: PRT
<213> ORGANISM: Lactobacillus plantarum

<400> SEQUENCE: 1

Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Glu Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Asp Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Ile Ile Gly Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320

<210> SEQ ID NO 2
```

<211> LENGTH: 963
<212> TYPE: DNA
<213> ORGANISM: Lactobacillus plantarum

<400> SEQUENCE: 2

| | | | | | |
|---|---|---|---|---|---|
| atgtcttcta | tgccaaatca | tcaaaaagtt | gttttggttg | gtgatggtgc | tgttggttct | 60 |
| tcttatgctt | ttgctatggc | tcaacaaggt | attgctgaag | aatttgttat | tgttgatgtt | 120 |
| gttaaagata | gaactaaagg | tgatgctttg | gatttggaag | atgctcaagc | ttttactgct | 180 |
| ccaaaaaaaa | tttattctgg | tgaatattct | gattgtaaag | atgctgattt | ggttgttatt | 240 |
| actgctggtg | ctccacaaaa | accaggtgaa | tctagattgg | atttggttaa | taaaaatttg | 300 |
| aatattttgt | cttctattgt | taaaccagtt | gttgattctg | gttttgatgg | tattttttg | 360 |
| gttgctgcta | tccagttga | tattttgact | tatgctactt | ggaaattttc | tggttttcca | 420 |
| aaagaaagag | ttattggttc | tggtacttct | ttggattctt | ctagattgag | agttgctttg | 480 |
| ggtaaacaat | taatgttga | tccaagatct | gttgatgctt | atattatggg | tgaacatggt | 540 |
| gattctgaat | tgctgctta | ttctactgct | actattggta | ctagaccagt | tagagatgtt | 600 |
| gctaaagaac | aaggtgtttc | tgatgatgat | ttggctaaat | tggaagatgg | tgttagaaat | 660 |
| aaagcttatg | atattattaa | tttgaaaggt | gctacttttt | atggtattgg | tactgctttg | 720 |
| atgagaattt | ctaaagctat | tttgagagat | gaaaatgctg | ttttgccagt | tggtgcttat | 780 |
| atggatggtc | aatatggttt | gaatgatatt | tatattggta | ctccagctat | tattggtggt | 840 |
| actggtttga | acaaattat | tgaatctcca | ttgtctgctg | atgaattgaa | aaaaatgcaa | 900 |
| gattctgctg | ctactttgaa | aaagttttg | atgatggtt | tggctgaatt | ggaaaataaa | 960 |
| taa | | | | | | 963 |

<210> SEQ ID NO 3
<211> LENGTH: 988
<212> TYPE: DNA
<213> ORGANISM: Artificial Sequence
<220> FEATURE:
<223> OTHER INFORMATION: g4423 promotor region Allele 1

<400> SEQUENCE: 3

| | | | | | |
|---|---|---|---|---|---|
| gttaactcag | ttttctctct | ttccctccac | cccacgttac | tctgcgaaca | aaaatacgca | 60 |
| cagaatgaac | atctgattga | ttaatattta | tatattactt | agtggcaccc | ctacaaacaa | 120 |
| accaattttg | aatatttctc | accatcatga | tatttattta | gggcaagaat | tcatgtaca | 180 |
| tacgtgcgtg | tactgcatag | ttttgttata | tgtaaataac | cagcaatata | tcaccaatga | 240 |
| taaatgctca | gtaatttatt | tggaaccaaa | atagtttcag | taatcaaata | atacaataac | 300 |
| taacaagtgc | tgattataca | acagctgtta | acaacacaaa | cacgctctct | tctattctct | 360 |
| tccctgcttg | ttcgtgtggt | atattcccga | atttgcaatt | tagaaattat | attttttaaa | 420 |
| agaattgttc | tccatttct | ggtagtcgta | agtggcaaat | tggatcataa | gacacaatct | 480 |
| tgttagttcg | actgctaaca | ccagacaaga | ccgaacgaaa | acagaaaaaa | aagataaattt | 540 |
| tgttattctg | ttcaattctc | tctctcttttt | taaggtatct | ttacattaca | ttacatatcc | 600 |
| caaattacaa | caagagcaag | aaatgaagca | caacaacacg | ccatctttcg | tgattatttt | 660 |
| atcatttcta | tatcgtaact | aaattaacaa | atgctatgtt | tcttaatttt | taatgataaa | 720 |
| tctaactgct | accttaattt | ctcatggaaa | gtggcaaata | cagaaattat | atattcttat | 780 |
| tcatttttctt | ataattttta | tcaattacca | aatatatata | aatgcaatta | attgattgtt | 840 |
| cctgtcacat | aatttttttt | gtttgttacc | tttattcttt | atccatttag | tttagttctt | 900 |

| | | |
|---|---|---|
| atatctttct tttctatttc tcttttcgt ttaatctcac cgtacacata tatatccata | 960 | |
| tatcaataca aataaaaatc atttaaaa | 988 | |

<210> SEQ ID NO 4
<211> LENGTH: 961
<212> TYPE: DNA
<213> ORGANISM: Artificial Sequence
<220> FEATURE:
<223> OTHER INFORMATION: g4423 promotor region Allele 2

<400> SEQUENCE: 4

| | |
|---|---|
| gttaactcag ttttctctct ttccctccac cccacgttac tctgcgaaca aaaaatacgc | 60 |
| acagaatgaa catctgattg attaatattt atatattact cagtggcacc cctacaaaca | 120 |
| aaccaatttt gaatattgtt caccatcatg atatttattt agggcaagaa tttcatgtac | 180 |
| atacgtgcgt gtactgcata gttttgttat atgaaaataa ccagcaatat atcaccaatg | 240 |
| aataaattct caataattta tttggaacca aataatgcaa taactagcaa actaagtggt | 300 |
| gattatacaa cagctgttaa caacacaaac atacgctctc ttctattatc tcttccctgc | 360 |
| ttgttcgtgt ggtatattca cgaatttgca atttagaaat tatatttttt aaaagaattg | 420 |
| ttctccattt tctggtagtc gtaagtggca aattggatca taagacacaa tcttgttagt | 480 |
| tcgactgcta acaccagaca acaccgaacg aaaacaagaa aaaataatta ttctctctct | 540 |
| ttttaaggta tcttacatta catatcccaa attacaacaa gagcaagaaa tgaggcacaa | 600 |
| caacacacca tcatctttcg tgattatttt tatcatttct atcatgtaat taaattaaca | 660 |
| aatgttaagt ttattaattt ttaatgataa atctagttgc taccttaatt tctcatggaa | 720 |
| agtggcaaat actgaaatta tttaattcta cttcatttt cttataattt ttatcaatta | 780 |
| ccaaatatat ataaatgcaa ttaattgatt gttcctgtca cataatttt tttgtttgtt | 840 |
| acctttattc tttatccatt taatttattt cttgtatctt tcttttctat ttctcttttc | 900 |
| tgtttaatct caccgtacac atatatatcc atatatcaat acaaataaaa atcatttaaa | 960 |
| a | 961 |

<210> SEQ ID NO 5
<211> LENGTH: 1017
<212> TYPE: DNA
<213> ORGANISM: Artificial Sequence
<220> FEATURE:
<223> OTHER INFORMATION: g4423 terminator region Allele 1

<400> SEQUENCE: 5

| | |
|---|---|
| taagtcattt aatttattct tttagaatat atttattttg tctttatttt tgaaatgtta | 60 |
| atagtctttt ttttttactt tgaacaaaaa aaagtaaaat taaaacttat cttatatacg | 120 |
| cttttaaaca ttaaactcgt taacgaatta tataatgatt ttatcgaact actttatgtt | 180 |
| tttttaatag aataatcttc tttattaata taacttacta cttcttaatc ttgttgtcct | 240 |
| ccattcgaaa ctcgagtgga acattttctg agtatctctc gcgtctgttc gtaccgtttt | 300 |
| tccaatttct ttcgggaaac ggaactggac gcatttatt tgactgttga aagggagatt | 360 |
| taatatttat atagcgagat ataacaacta acttataagt ttacacaggc tgttatcaca | 420 |
| tatatatata tatatcaaca gaggactagc tcactagact aacattagat atgtcgatgc | 480 |
| tgaaccgttt gttggtgtt agatccattt cacaatgtgc tactcgttta caacgttcta | 540 |
| cagggacaaa tatatcagaa ggtccactaa gaattattcc acaattacaa actttctatt | 600 |

| | |
|---|---|
| ctgctaatcc aatgcatgat aacaatatcg acaagctaga aaatcttcta cgtaaatata | 660 |
| tcaagttacc aagtacaaac aatttattga agacacatgg gaatacatct acagaaattg | 720 |
| atccaacaaa attattacaa tcacaaaatt cttcacgtcc tttatggtta tcattcaagg | 780 |
| attatacagt gattggaggt ggttcacgtt taaaacctac tcaatacacg gaacttttat | 840 |
| ttctattgaa taaactacat agtatcgatc cacaattaat gaatgatgat attaagaacg | 900 |
| aattagctca ttattataag aatacttcac aggaaactaa taaagtcacc atccctaaat | 960 |
| tggatgaatt cggtagaagt attggaatcg gtagaaggaa atccgcaact gcaaaag | 1017 |

<210> SEQ ID NO 6
<211> LENGTH: 1018
<212> TYPE: DNA
<213> ORGANISM: Artificial Sequence
<220> FEATURE:
<223> OTHER INFORMATION: g4423 terminator region Allele 2

<400> SEQUENCE: 6

| | |
|---|---|
| taagtcattt aatttattct tttagaatat atttattttg tctttatttt tgaaatgtta | 60 |
| atagtctttt ttttactttg aaaaaaaaaa aaagtaaaat taaacttatc ttatatacgc | 120 |
| ttttaaacat taaactcgtt aacgaattat ataatgattt tatcgaacta ctttatgttt | 180 |
| ttttaataga ataatcttct ttattaatat aacttactac ttcttaatct tgttgtcctc | 240 |
| cattcgaaac tcgagaggaa caatttctga gtctctctcg caccctttcg tacgtaccgt | 300 |
| ttttccaatt tctttcggga aacggaactg gacgcatttt atttgactgt tgaaagggag | 360 |
| atttaatatt tatatagaga gatataacaa ctaacttata agtttataca ggctgttatc | 420 |
| acatatatat atatatcaac agaggactag ctcaatagaa taacattaga tatgtcgatg | 480 |
| ctgaaccgtt tgtttggtgt tagatccatt tcacaatgtg ctactcgttt acaacgttct | 540 |
| acagggacaa atatatcaga aggtccacta agaattattc cacaattaca aactttctat | 600 |
| tctgctaatc caatgcatga taacaatatc gacaagctag aaaatcttct acgtaaatat | 660 |
| atcaagttac caagtacaaa taacttattg aagacacatg ggaatacatc tacagaaatc | 720 |
| gatccaacaa aattattaca atcacaaaat tcttcacgtc ctttatggtt atcattcaag | 780 |
| gattatacag tgattggagg tggttcacgt ttaaaaccta ctcaatacac ggaacttta | 840 |
| tttctattga ataaactaca tagtatcgat ccacaattaa tgaatgatga tattaagaac | 900 |
| gaattagctc attattataa gaatacttca caggaaacta taaagtcac catccctaaa | 960 |
| ttggatgaat tcggtagaag tattggaatc ggtagaagga aatccgcaac tgcaaaag | 1018 |

<210> SEQ ID NO 7
<211> LENGTH: 323
<212> TYPE: PRT
<213> ORGANISM: Lactobacillus helveticus

<400> SEQUENCE: 7

Met Ala Arg Glu Glu Lys Pro Arg Lys Val Ile Leu Val Gly Asp Gly
1               5                   10                  15

Ala Val Gly Ser Thr Phe Ala Phe Ser Met Val Gln Gln Gly Ile Ala
            20                  25                  30

Glu Glu Leu Gly Ile Ile Asp Ile Ala Lys Glu His Val Glu Gly Asp
        35                  40                  45

Ala Ile Asp Leu Ala Asp Ala Thr Pro Trp Thr Ser Pro Lys Asn Ile
    50                  55                  60

Tyr Ala Ala Asp Tyr Pro Asp Cys Lys Asp Ala Asp Leu Val Val Ile

```
                65                  70                  75                  80
Thr Ala Gly Ala Pro Gln Lys Pro Gly Glu Thr Arg Leu Asp Leu Val
                    85                  90                  95

Asn Lys Asn Leu Lys Ile Leu Ser Ser Ile Val Glu Pro Val Val Glu
                100                 105                 110

Ser Gly Phe Glu Gly Ile Phe Leu Val Val Ala Asn Pro Val Asp Ile
            115                 120                 125

Leu Thr His Ala Thr Trp Arg Met Ser Gly Phe Pro Lys Asp Arg Val
        130                 135                 140

Ile Gly Ser Gly Thr Ser Leu Asp Thr Gly Arg Leu Gln Lys Val Ile
145                 150                 155                 160

Gly Lys Met Glu Asn Val Asp Pro Ser Ser Val Asn Ala Tyr Met Leu
                165                 170                 175

Gly Glu His Gly Asp Thr Glu Phe Pro Ala Trp Ser Tyr Asn Asn Val
            180                 185                 190

Ala Gly Val Lys Val Ala Asp Trp Val Lys Ala His Asn Met Pro Glu
        195                 200                 205

Ser Lys Leu Glu Asp Ile His Gln Glu Val Lys Asp Met Ala Tyr Asp
    210                 215                 220

Ile Ile Asn Lys Lys Gly Ala Thr Phe Tyr Gly Ile Gly Thr Ala Ser
225                 230                 235                 240

Ala Met Ile Ala Lys Ala Ile Leu Asn Asp Glu His Arg Val Leu Pro
                245                 250                 255

Leu Ser Val Pro Met Asp Gly Glu Tyr Gly Leu His Asp Leu His Ile
            260                 265                 270

Gly Thr Pro Ala Val Val Gly Arg Lys Gly Leu Glu Gln Val Ile Glu
        275                 280                 285

Met Pro Leu Ser Asp Lys Glu Gln Glu Leu Met Thr Ala Ser Ala Asp
    290                 295                 300

Gln Leu Lys Lys Val Met Asp Lys Ala Phe Lys Glu Thr Gly Val Lys
305                 310                 315                 320

Val Arg Gln

<210> SEQ ID NO 8
<211> LENGTH: 972
<212> TYPE: DNA
<213> ORGANISM: Lactobacillus helveticus

<400> SEQUENCE: 8
atggctagag aagaaaaacc aagaaaagtt attttggttg gtgatggtgc tgttggttct      60
acttttgctt tttctatggt tcaacaaggt attgctgaag aattgggtat tattgatatt     120 gctaagaac atgttgaagg tgatgctatt gatttggctg atgctactcc atggacttct     180
ccaaaaaata tttatgctgc tgattatcca gattgtaaag atgctgattt ggttgttatt     240
actgctggtg ctccacaaaa accaggtgaa actagattgg atttggttaa taaaaatttg     300
aaaattttgt cttctattgt tgaaccagtt gttgaatctg gttttgaagg tatttttttg     360
gttgttgcta atccagttga tattttgact catgctactt ggagaatgtc tggttttcca     420
aaagatagag ttattggttc tggtacttct ttggatactg gtagattgca aaaagttatt     480
ggtaaaatgg aaaatgttga tccatcttct gttaatgctt atatgttggg tgaacatggt     540
gatactgaat ttccagcttg gtcttataat aatgttgctg gtgttaaagt tgctgattgg     600
gttaaagctc ataatatgcc agaatctaaa ttggaagata ttcatcaaga agttaaagat     660
```

```
atggcttatg atattattaa taaaaaaggt gctactttt atggtattgg tactgcttct    720
gctatgattg ctaaagctat tttgaatgat gaacatagag ttttgccatt gtctgttcca    780
atggatggtg aatatggttt gcatgatttg catattggta ctccagctgt tgttggtaga    840
aaaggtttgg aacaagttat tgaaatgcca ttgtctgata agaacaaga attgatgact     900 gcttctgctg atcaattgaa aaaagttatg gataaagctt ttaaagaaac tggtgttaaa    960
gttagacaat aa                                                        972
```

<210> SEQ ID NO 9
<211> LENGTH: 320
<212> TYPE: PRT
<213> ORGANISM: Rhizopus oryzae

<400> SEQUENCE: 9

```
Met Val Leu His Ser Lys Val Ala Ile Val Gly Ala Gly Ala Val Gly
1               5                   10                  15

Ala Ser Thr Ala Tyr Ala Leu Met Phe Lys Asn Ile Cys Thr Glu Ile
            20                  25                  30

Ile Ile Val Asp Val Asn Pro Asp Ile Val Gln Ala Gln Val Leu Asp
        35                  40                  45

Leu Ala Asp Ala Ala Ser Ile Ser His Thr Pro Ile Arg Ala Gly Ser
    50                  55                  60

Ala Glu Glu Ala Gly Gln Ala Asp Ile Val Val Ile Thr Ala Gly Ala
65                  70                  75                  80

Lys Gln Arg Glu Gly Glu Pro Arg Thr Lys Leu Ile Glu Arg Asn Phe
                85                  90                  95

Arg Val Leu Gln Ser Ile Ile Gly Gly Met Gln Pro Ile Arg Pro Asp
            100                 105                 110

Ala Val Ile Leu Val Val Ala Asn Pro Val Asp Ile Leu Thr His Ile
        115                 120                 125

Ala Lys Thr Leu Ser Gly Leu Pro Pro Asn Gln Val Ile Gly Ser Gly
    130                 135                 140

Thr Tyr Leu Asp Thr Thr Arg Leu Arg Val His Leu Gly Asp Val Phe
145                 150                 155                 160

Asp Val Asn Pro Gln Ser Val His Ala Phe Val Leu Gly Glu His Gly
                165                 170                 175

Asp Ser Gln Met Ile Ala Trp Glu Ala Ala Ser Ile Gly Gly Gln Pro
            180                 185                 190

Leu Thr Ser Phe Pro Glu Phe Ala Lys Leu Asp Lys Thr Ala Ile Ser
        195                 200                 205

Lys Ala Ile Ser Gly Lys Ala Met Glu Ile Ile Arg Leu Lys Gly Ala
    210                 215                 220

Thr Phe Tyr Gly Ile Gly Ala Cys Ala Ala Asp Leu Val His Thr Ile
225                 230                 235                 240

Met Leu Asn Arg Lys Ser Val His Pro Val Ser Val Tyr Val Glu Lys
                245                 250                 255

Tyr Gly Ala Thr Phe Ser Met Pro Ala Lys Leu Gly Trp Arg Gly Val
            260                 265                 270

Glu Gln Ile Tyr Glu Val Pro Leu Thr Glu Glu Glu Ala Leu Leu
        275                 280                 285

Val Lys Ser Val Glu Ala Leu Lys Ser Val Glu Tyr Ser Ser Thr Lys
    290                 295                 300

Val Pro Glu Lys Lys Val His Ala Thr Ser Phe Ser Lys Ser Ser Cys
305                 310                 315                 320
```

-continued

```
<210> SEQ ID NO 10
<211> LENGTH: 963
<212> TYPE: DNA
<213> ORGANISM: Rhizopus oryzae

<400> SEQUENCE: 10
atggttttgc attctaaagt tgctattgtt ggtgctggtg ctgttggtgc ttctactgct      60
tatgctttga tgtttaaaaa tatttgtact gaaattatta ttgttgatgt taatccagat    120
attgttcaag ctcaagtttt ggatttggct gatgctgctt ctatttctca tactccaatt    180
agagctggtt ctgctgaaga agctggtcaa gctgatattg ttgttattac tgctggtgct    240
aaacaaagag aaggtgaacc aagaactaaa ttgattgaaa gaatttttag agttttgcaa    300
tctattattg gtggtatgca accaattaga ccagatgctg ttattttggt tgttgctaat    360
ccagttgata ttttgactca tattgctaaa actttgtctg gtttgccacc aaatcaagtt    420
attggttctg gtacttattt ggatactact agattgagag ttcatttggg tgatgttttt    480
gatgttaatc cacaatctgt tcatgctttt gttttgggtg aacatggtga ttctcaaatg    540
attgcttggg aagctgcttc tattggtggt caaccattga cttcttttcc agaatttgct    600
aaattggata aaactgctat ttctaaagct atttctggta agctatggaa aattattaga    660
ttgaaaggtg ctacttttta tggtattggt gcttgtgctg ctgatttggt tcatactatt    720
atgttgaata gaaaatctgt tcatccagtt tctgtttatg ttgaaaaata tggtgctact    780 tttttctatgc cagctaaatt gggttggaga ggtgttgaac aaatttatga agttccattg    840
actgaagaag aagaagcttt gttggttaaa tctgttgaag ctttgaaatc tgttgaatat    900
tcttctacta agttccaga aaaaaaagtt catgctactt cttttctaa atcttcttgt      960 taa                                                                 963

<210> SEQ ID NO 11
<211> LENGTH: 22
<212> TYPE: DNA
<213> ORGANISM: Artificial Sequence
<220> FEATURE:
<223> OTHER INFORMATION: primer for qPCR

<400> SEQUENCE: 11
cggactttag agccttgtag ac                                             22

<210> SEQ ID NO 12
<211> LENGTH: 21
<212> TYPE: DNA
<213> ORGANISM: Artificial Sequence
<220> FEATURE:
<223> OTHER INFORMATION: primer for qPCR

<400> SEQUENCE: 12
atctggttac actcacgatg g                                              21

<210> SEQ ID NO 13
<211> LENGTH: 22
<212> TYPE: DNA
<213> ORGANISM: Artificial Sequence
<220> FEATURE:
<223> OTHER INFORMATION: primer for qPCR

<400> SEQUENCE: 13
ccaagtacgt tagagctaac gg                                             22
```

<210> SEQ ID NO 14
<211> LENGTH: 20
<212> TYPE: DNA
<213> ORGANISM: Artificial Sequence
<220> FEATURE:
<223> OTHER INFORMATION: primer for qPCR

<400> SEQUENCE: 14
gagcttctct ggtatcagct                                       20

<210> SEQ ID NO 15
<211> LENGTH: 22
<212> TYPE: DNA
<213> ORGANISM: Artificial Sequence
<220> FEATURE:
<223> OTHER INFORMATION: primer for qPCR

<400> SEQUENCE: 15
agctttagca aacattagac cc                                    22

<210> SEQ ID NO 16
<211> LENGTH: 21
<212> TYPE: DNA
<213> ORGANISM: Artificial Sequence
<220> FEATURE:
<223> OTHER INFORMATION: primer for qPCR

<400> SEQUENCE: 16
attccatccg aatatgctgg t                                     21

<210> SEQ ID NO 17
<211> LENGTH: 22
<212> TYPE: DNA
<213> ORGANISM: Artificial Sequence
<220> FEATURE:
<223> OTHER INFORMATION: primer for qPCR

<400> SEQUENCE: 17
ggaacctaaa tgactgttgg ca                                    22

<210> SEQ ID NO 18
<211> LENGTH: 21
<212> TYPE: DNA
<213> ORGANISM: Artificial Sequence
<220> FEATURE:
<223> OTHER INFORMATION: primer for qPCR

<400> SEQUENCE: 18
aggatgttga tttcgactcg t                                     21

<210> SEQ ID NO 19
<211> LENGTH: 24
<212> TYPE: DNA
<213> ORGANISM: Artificial Sequence
<220> FEATURE:
<223> OTHER INFORMATION: primer for qPCR

<400> SEQUENCE: 19
ttccaaaggg taccaattta gctg                                  24

<210> SEQ ID NO 20
<211> LENGTH: 23
<212> TYPE: DNA
<213> ORGANISM: Artificial Sequence
<220> FEATURE:
<223> OTHER INFORMATION: primer for qPCR

<400> SEQUENCE: 20
gtaccgctaa tgaacctaaa cca                                            23

<210> SEQ ID NO 21
<211> LENGTH: 21
<212> TYPE: DNA
<213> ORGANISM: Artificial Sequence
<220> FEATURE:
<223> OTHER INFORMATION: primer for qPCR

<400> SEQUENCE: 21
agagctgaca ctagagaagc c                                              21

<210> SEQ ID NO 22
<211> LENGTH: 23
<212> TYPE: DNA
<213> ORGANISM: Artificial Sequence
<220> FEATURE:
<223> OTHER INFORMATION: primer for qPCR

<400> SEQUENCE: 22
gatgtgtcta cgacgtatct acc                                            23

<210> SEQ ID NO 23
<211> LENGTH: 20
<212> TYPE: DNA
<213> ORGANISM: Artificial Sequence
<220> FEATURE:
<223> OTHER INFORMATION: primer for qPCR

<400> SEQUENCE: 23
gtactggtaa cgtccaagtc                                                20

<210> SEQ ID NO 24
<211> LENGTH: 21
<212> TYPE: DNA
<213> ORGANISM: Artificial Sequence
<220> FEATURE:
<223> OTHER INFORMATION: primer for qPCR

<400> SEQUENCE: 24
gaacccttcc atactctacc a                                              21

<210> SEQ ID NO 25
<211> LENGTH: 21
<212> TYPE: DNA
<213> ORGANISM: Artificial Sequence
<220> FEATURE:
<223> OTHER INFORMATION: primer for qPCR

<400> SEQUENCE: 25
ttcagttcgt gctactcaag g                                              21

<210> SEQ ID NO 26
<211> LENGTH: 20
<212> TYPE: DNA
<213> ORGANISM: Artificial Sequence
<220> FEATURE:
<223> OTHER INFORMATION: primer for qPCR

<400> SEQUENCE: 26
tcaattgcaa cgacagagac                                                20

<210> SEQ ID NO 27

<211> LENGTH: 22
<212> TYPE: DNA
<213> ORGANISM: Artificial Sequence
<220> FEATURE:
<223> OTHER INFORMATION: primer for qPCR

<400> SEQUENCE: 27
ccgtaccctg aagagtttac tg                                    22

<210> SEQ ID NO 28
<211> LENGTH: 24
<212> TYPE: DNA
<213> ORGANISM: Artificial Sequence
<220> FEATURE:
<223> OTHER INFORMATION: primer for qPCR

<400> SEQUENCE: 28
caaccataga ttcacgaatt gctc                                  24

<210> SEQ ID NO 29
<211> LENGTH: 22
<212> TYPE: DNA
<213> ORGANISM: Artificial Sequence
<220> FEATURE:
<223> OTHER INFORMATION: primer for qPCR

<400> SEQUENCE: 29
agtggatttg gattaatggg tg                                    22

<210> SEQ ID NO 30
<211> LENGTH: 22
<212> TYPE: DNA
<213> ORGANISM: Artificial Sequence
<220> FEATURE:
<223> OTHER INFORMATION: primer for qPCR

<400> SEQUENCE: 30
gcttctgtaa cacctttaac ac                                    22

<210> SEQ ID NO 31
<211> LENGTH: 20
<212> TYPE: DNA
<213> ORGANISM: Artificial Sequence
<220> FEATURE:
<223> OTHER INFORMATION: primer for qPCR

<400> SEQUENCE: 31
aaattggtga ccgtgttggt                                       20

<210> SEQ ID NO 32
<211> LENGTH: 23
<212> TYPE: DNA
<213> ORGANISM: Artificial Sequence
<220> FEATURE:
<223> OTHER INFORMATION: primer for qPCR

<400> SEQUENCE: 32
aaccaccttt actacggtaa cca                                   23

<210> SEQ ID NO 33
<211> LENGTH: 22
<212> TYPE: DNA
<213> ORGANISM: Artificial Sequence
<220> FEATURE:
<223> OTHER INFORMATION: primer for qPCR

<400> SEQUENCE: 33
tttagtcgtc atctgttcag gt                                            22

<210> SEQ ID NO 34
<211> LENGTH: 23
<212> TYPE: DNA
<213> ORGANISM: Artificial Sequence
<220> FEATURE:
<223> OTHER INFORMATION: primer for qPCR

<400> SEQUENCE: 34
gagacaccta acaaaccaaa tgg                                           23

<210> SEQ ID NO 35
<211> LENGTH: 24
<212> TYPE: DNA
<213> ORGANISM: Artificial Sequence
<220> FEATURE:
<223> OTHER INFORMATION: primer for qPCR

<400> SEQUENCE: 35
gattcaagct tcttctcgta tcgg                                          24

<210> SEQ ID NO 36
<211> LENGTH: 23
<212> TYPE: DNA
<213> ORGANISM: Artificial Sequence
<220> FEATURE:
<223> OTHER INFORMATION: primer for qPCR

<400> SEQUENCE: 36
ggaaatgata ccattcacga cct                                           23

<210> SEQ ID NO 37
<211> LENGTH: 22
<212> TYPE: DNA
<213> ORGANISM: Artificial Sequence
<220> FEATURE:
<223> OTHER INFORMATION: primer for qPCR

<400> SEQUENCE: 37
gttccgtcaa agaaatcaag ca                                            22

<210> SEQ ID NO 38
<211> LENGTH: 24
<212> TYPE: DNA
<213> ORGANISM: Artificial Sequence
<220> FEATURE:
<223> OTHER INFORMATION: primer for qPCR

<400> SEQUENCE: 38
tggtaaacct gtatctgaca tcac                                          24

<210> SEQ ID NO 39
<211> LENGTH: 22
<212> TYPE: DNA
<213> ORGANISM: Artificial Sequence
<220> FEATURE:
<223> OTHER INFORMATION: primer for qPCR

<400> SEQUENCE: 39
tttagttgtc atttgtgccg gt                                            22

<210> SEQ ID NO 40
<211> LENGTH: 22
<212> TYPE: DNA

<213> ORGANISM: Artificial Sequence
<220> FEATURE:
<223> OTHER INFORMATION: primer for qPCR

<400> SEQUENCE: 40
gacacctaac aaaccaaacg ga                                              22

<210> SEQ ID NO 41
<211> LENGTH: 20
<212> TYPE: DNA
<213> ORGANISM: Artificial Sequence
<220> FEATURE:
<223> OTHER INFORMATION: primer for qPCR

<400> SEQUENCE: 41
ctttgagtgc aagtatcgcc                                                 20

<210> SEQ ID NO 42
<211> LENGTH: 22
<212> TYPE: DNA
<213> ORGANISM: Artificial Sequence
<220> FEATURE:
<223> OTHER INFORMATION: primer for qPCR

<400> SEQUENCE: 42
tgtgtaattg ttcaccaaag cc                                              22

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
gagatagcac accattcacc a                                               21

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
caacgttaag tactctggtg tttg                                            24

<210> SEQ ID NO 45
<211> LENGTH: 24
<212> TYPE: DNA
<213> ORGANISM: Artificial Sequence
<220> FEATURE:
<223> OTHER INFORMATION: primer

<400> SEQUENCE: 45
caacgttaag tactctggtg tttg                                            24

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
gagatagcac accattcacc a                                               21

<210> SEQ ID NO 47
<211> LENGTH: 24
<212> TYPE: DNA
<213> ORGANISM: Artificial Sequence
<220> FEATURE:
<223> OTHER INFORMATION: primer

<400> SEQUENCE: 47
ggattcctgt aatgacaacg cgag                                    24

<210> SEQ ID NO 48
<211> LENGTH: 26
<212> TYPE: DNA
<213> ORGANISM: Artificial Sequence
<220> FEATURE:
<223> OTHER INFORMATION: primer

<400> SEQUENCE: 48
tggatacatt acagattctc tatcct                                  26

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
atgaaaattt ttgcttatgg                                         20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ttaatattca acagcaatag                                         20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
atggttttgc attctaaagt                                         20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ttaacaagaa gatttagaaa                                         20

<210> SEQ ID NO 53
<211> LENGTH: 20
<212> TYPE: DNA
<213> ORGANISM: Artificial Sequence
<220> FEATURE:

```
<223> OTHER INFORMATION: primer

<400> SEQUENCE: 53
atgtcttcta tgccaaatca                                        20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
ttatttattt tccaattcag                                        20
```

ACID-RESISTANT YEAST WITH SUPPRESSED ETHANOL PRODUCTION PATHWAY AND METHOD FOR PRODUCING LACTIC ACID USING SAME

CROSS REFERENCE TO RELATED APPLICATIONS

This application is a national phase of PCT application No. PCT/KR2019/002433, filed Feb. 28, 2019, which claims priority to KR patent application No. 1020180044509 filed Apr. 17, 2018, all of which are incorporated herein by reference thereto.

SEQUENCE LISTING

The instant application contains a Sequence Listing which has been submitted in ASCII format via EFS-Web and is hereby incorporated by reference in its entirety. Said ASCII copy, created on Oct. 15, 2020, is named 216871 PFB2479 ST25 Seq.txt and is 26,978 bytes in size.

TECHNICAL FIELD

The present invention relates to a method of producing lactic acid using an acid-resistant yeast having an inhibited ethanol production pathway, and more particularly to an acid-resistant yeast which is imparted with lactic-acid-producing ability and has an inhibited ethanol production pathway, and a method of producing lactic acid using the same.

BACKGROUND ART

Polylactic acid (PLA) is a biodegradable polymer that is prepared by converting lactic acid into lactide and conducting ring-opening polymerization thereon. The raw material thereof, lactic acid, is produced through fermentation. PLA is widely used in disposable food containers, and has a strength in that it is capable of being used alone or in the form of a composition or a copolymer in plastics for a variety of industries including the automobile industry. In addition, it is a representative polymer that has come to be used in 3D printing in recent years, and is an eco-friendly polymer that generates lower amounts of harmful gas and odors when used for 3D printers. This biodegradable polymer is a promising polymer that can reduce acceleration of environmental destruction by waste plastics and microplastics, which has become a global problem in recent years, and the use thereof is increasing in advanced countries. In order to produce PLA at a lower cost, efforts are being made to improve the productivity of lactic acid as a monomer.

A traditional lactic acid production process is performed using lactic acid bacteria, and includes conducting fermentation while maintaining a neutral pH of 6 to 8 using various forms of Ca salt or a neutralizing agent such as ammonia in order to prevent bacterial death or slowing of growth thereof due to lactic acid produced and accumulated by lactic acid bacteria. When fermentation is completed, microorganisms are separated, and sulfuric acid is added to convert lactate to lactic acid while Ca salt is removed in the form of $CaSO_4$ due to the difficulty of separation of salt from water and conversion thereof to lactide. In this process, $CaSO_4$, a byproduct, is produced in an amount greater than the amount of lactic acid, thus deteriorating process efficiency.

Meanwhile, lactate has L- and D-type optical isomers. There are a variety of microbial groups. For example, lactic acid bacteria that mainly produce L-type optical isomers often also produce about 5-10% of D-type optical isomers, and strains that mainly produce D-type optical isomers include strains that produce both D-type and L-type optical isomers, strains that produce both D-type optical isomers and ethanol, and the like (Ellen I. Garvie, Microbiological Reviews, 106-139, 1980).

Among these optically isomeric lactates, D-type was mainly used only for medical and drug delivery, but when applied to PLA, as the crystallization rate increases due to D-type lactide, an improvement in thermal properties is observed. When stereocomplex PLA is structurally formed according to combination processing conditions of pure L-type polymer and pure D-type polymer, new polymers with higher heat resistance than PE/PP as well as conventional PLA are discovered. As such, research and commercialization on increase in crystallinity due to D-type and improvement in physical properties of PLA through the same are actively underway and the range of fields in which PLA is applied is expanding.

In general, PLA produces lactic acid through fermentation, and then converts the produced lactic acid into lactide through a purification process. For conversion to lactide, a process of converting lactic acid into a hydrogenated form is required, and the pH for neutral fermentation is generally 6 to 7, and the neutral pH is thus changed to an acidic pH using a large amount of sulfuric acid. In this process, a large amount of neutralization salts is generated, and economic feasibility is deteriorated due to the low value of the neutralization salts along with the cost of investing in processes to remove the neutralization salts.

Meanwhile, in the case of *Lactobacillus*, which produces lactic acid in nature, a large amount of expensive nutrients must be used as a medium in order to commercially produce lactic acid. This excess of nutrient components greatly inhibits a downstream polymerization process or a lactide conversion process, or in the case in which lactide is used as an intermediate, costs for purification processes such as adsorption, distillation and ion exchange are incurred in order to obtain high-yield and high-purity polymers or precursors thereof, thus further increasing production costs. Research on the use of yeast has been suggested in order to solve these problems. Yeast is known to conduct growth/fermentation even when inexpensive nutrients are used, and to be highly resistant to acidic conditions.

When lactic acid is produced using yeast that grows well in acid (hereinafter referred to as "acid-resistant yeast"), it is not necessary to maintain the medium at a pH of 6 to 7 using a neutralizing agent during fermentation, so the fermentation process is simplified and a downstream purification process for removing the neutralizing agent is not required. In addition, yeast itself produces many components that it requires for metabolism, and thus can be cultured in a medium with a relatively low nutrient level compared to bacteria, particularly *Lactobacillus*, thus obviating downstream purification processes and significantly lowering production costs.

However, there is a prerequisite for technology for producing lactic acid using yeast. The prerequisite is that the yield, productivity, and concentration of lactic acid, which are indicators for strain fermentation performance, must be maintained at high levels similar to the performance of lactic acid bacteria in order for the technology to be commercially applied.

Although a number of documents claim the development of acid-resistant lactic acid technology using yeast, in practice, in many cases, high-performance fermentation capability is obtained only when fermentation is performed while maintaining a pH of at least 3.7, which is not less than the pKa value of lactic acid, by performing a neutralization reaction during the fermentation. For this reason, it is not reasonable to determine that the technology is a practical method for achieving acid resistance, and it is difficult to anticipate an effect of reducing production costs when applied to a process (Michael Sauer et al., *Biotechnology and Genetic Engineering Reviews*, 27:229-256, 2010).

Therefore, acid-resistant yeasts capable of reducing processing costs can realize commercial application only when they are capable of completing fermentation at a pH of a fermentation solution not more than the pKa value, without using a neutralizing agent or using the same in a minimum amount, and three major fermentation indicators achieve a level similar to that of lactic acid bacteria.

In general, yeast metabolizes ethanol as a main product when glucose is fermented, and produces hardly any lactic acid. In addition, since the probability of selecting a strain that produces lactic acid from microorganisms having high acid resistance is very low, the present inventors first selected a yeast strain having excellent acid resistance, and attempted to impart lactic acid production ability to the selected strain through a genetic-engineering method. In addition, all ethanol-producing strains were selected from the actually selected acid-resistant strain library.

The metabolic pathway for the production of lactic acid is carried out by a one-step reaction in pyruvate. This step is generated by the lactate dehydrogenase enzyme, and the lactic acid is then discharged to the outside of the cell through active transport or diffusion. In order to ferment such lactic acid as a main product, it is necessary to introduce lactic acid-producing ability and at the same time to perform an operation to remove the existing ethanol-producing ability. In general, the conversion of pyruvate to ethanol in yeast is carried out in a two-step reaction through acetaldehyde and a method including removing the PDC gene that converts pyruvate to acetaldehyde, and introducing LDH is generally used.

However, in the case of Crabtree-positive yeast such as *Saccharomyces cerevisiae*, when pyruvate decarboxylase (PDC) is completely blocked, the supply of cytosolic acetyl-CoA, which is required for the synthesis of lipids in cells, is blocked and thus growth is greatly inhibited. When PDC is not completely blocked, there occur problems in which ethanol production cannot be completely blocked due to competition with LDH for the same substrate, pyruvate, and thus yield cannot be increased to the level of lactic acid bacteria.

Accordingly, the present inventors have made intensive efforts to select an acid-resistant yeast and impart lactic acid production ability thereto. As a result, the present inventors have found that, when the ADH (alcohol dehydrogenase) gene of the metabolic pathway for ethanol production in the acid-resistant yeast is replaced with the LDH gene of the metabolic pathway for lactic acid production, the expression of LDH is remarkably increased, and thus the ability to produce lactic acid is increased. Based on this finding, the present invention has been completed.

Summary of the Invention

Therefore, the present invention has been made in view of the above problems, and it is one object of the present invention to provide a recombinant acid-resistant yeast having reduced ethanol production ability and improved lactic acid production ability.

It is another object of the present invention to provide a method of producing lactic acid using the recombinant acid-resistant yeast.

In accordance with one aspect of the present invention, the above and other objects can be accomplished by the provision of a recombinant strain having lactic-acid-producing ability, in which a g4423 gene is deleted or attenuated from an acid-resistant yeast YBC strain (KCTC13508BP) and a gene encoding a lactate dehydrogenase is introduced into the YBC strain.

In accordance with another aspect of the present invention, there is provided a method of producing lactic acid including (a) culturing the recombinant strain according to the present invention to produce lactic acid and (b) obtaining the produced lactic acid.

In accordance with another aspect of the present invention, there is provided a gene construct including a promoter comprising the nucleotide sequence of SEQ ID NO: 2 and a gene encoding lactate dehydrogenase operably linked to each other and a recombinant vector including the gene construct.

In accordance with another aspect of the present invention, there is provided a recombinant microorganism into which the genetic structure or the recombinant vector is introduced.

In accordance with another aspect of the present invention, there is provided a method of producing lactic acid including (a) culturing the recombinant strain according to the present invention to produce lactic acid, and (b) obtaining the produced lactic acid.

DETAILED DESCRIPTION OF PREFERRED EMBODIMENTS

Figure 1:
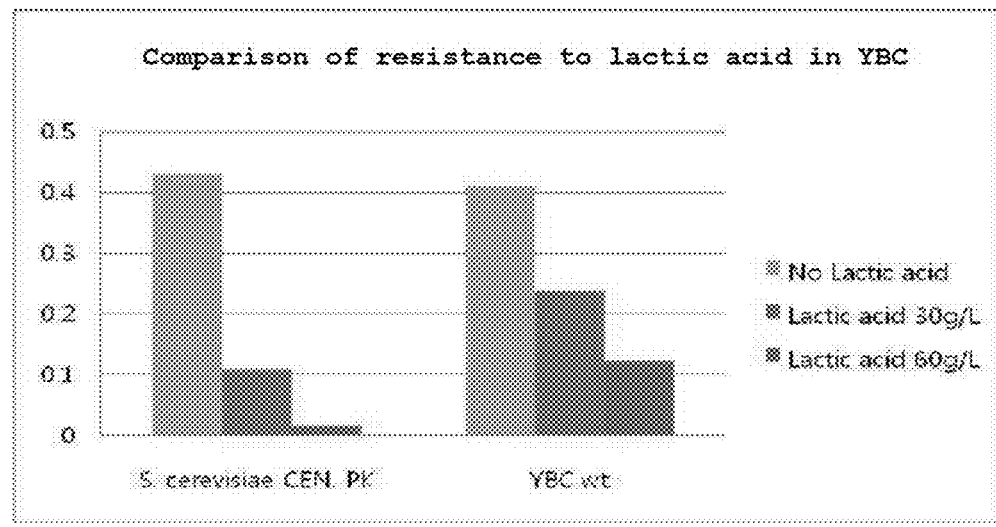
FIG. 1 shows the result of comparing the resistance to lactic acid between a conventionally known *S. cerevisiae* strain and a YBC strain as the acid-resistant strain used in the present invention.

Unless defined otherwise, all technical and scientific terms used herein have the same meanings as appreciated by those skilled in the field to which the present invention pertains. In general, the nomenclature used herein is well-known in the art and is ordinarily used.

Acid-resistant yeast is characterized by consuming sugar at a fast rate even at an acidic pH, exhibiting a high growth rate, and converting the consumed sugar into a desired product under fermentation conditions. In the present invention, the acid-resistant yeast is selected from among yeasts having these characteristics through several yeast libraries, and the selected strains had a high growth rate and a high sugar consumption rate even at a lactic acid concentration of 40 g/L to 80 g/L. The selected strains were subjected to metabolic pathway control using genetic engineering.

As stated in the description of the method for controlling metabolic pathways above, many researchers have conducted studies on reduction of ethanol by removing the pyruvate decarboxylase enzyme through competitive reaction in pyruvate, and many previous studies by Cargill, Toyota, Samsung and the like have been published (U.S. Pat. Nos. 7,534,597, 7,141,410B2, 9,353,388B2, JP 4692173B2, JP 2001-204464A, JP 4095889B2, and KR 1686900B1). The effect of reducing ethanol through the removal of PDC is very direct and effective, but yeast causes serious side effects due to removal of PDC. In particular, strains with very strong ethanol fermentation such as Crabtree-positive strains cause greater side effects (Yiming Zhang, et al., Microbial Cell Factory, 14:116, 2015). Acetyl-CoA, which is an essential metabolite in yeast, is supplied by the Pdh enzyme in mitochondria, but acetaldehyde is produced through the PDC pathway in metabolism from sugar in the cytoplasm. Therefore, when the PDC gene is removed, the supply of acetyl-CoA in the cytoplasm is stopped, and for this reason, the production of fatty acids is stopped and thus cell growth is inhibited. In Crabtree-positive strains in which respiration-related genes are inhibited by glucose and the TCA cycle in the mitochondria is weakened, this phenomenon is greatly strengthened. Such cytoplasmic acetyl-CoA may be supplied through other side reaction pathways, but the rate of production of fermentation products is inhibited due to severe growth inhibition, and thus the value thereof as a commercial strain is lost. In order to reduce these side effects, strains with the enhanced indirect supply pathway of acetyl-CoA should be produced through mutation/evolution, but such evolution requires long-term research, the effect thereof may be different for each strain, and the exact mechanism thereof has not been elucidated yet.

An alternative approach is to prevent the conversion of ethanol from acetaldehyde by blocking ADH as the next step of PDC. This method of blocking ADH does not inhibit growth due to insufficient supply of cytoplasmic acetyl-CoA, but inhibits growth through accumulation of acetaldehyde, which is a precursor of ethanol and a toxic substance, by blocking ADH. The accumulation of acetaldehyde by blocking ADH can be reduced by introducing the lactate metabolic pathway to be strongly expressed. Since lactate metabolism is carried out by conversion from pyruvate, which is an upstream reactant of acetaldehyde, as this pathway is strengthened, the flux to PDC and ADH naturally decreases, and this natural decrease in flux can reduce the accumulated concentration of acetaldehyde. Against this background, the present invention has developed a yeast strain that blocks ADH and increases lactate production.

Therefore, in one aspect, the present invention is directed to a recombinant strain having lactic-acid-producing ability, in which a g4423 gene is deleted or attenuated from an acid-resistant yeast YBC strain (KCTC13508BP) and a gene encoding a lactate dehydrogenase is introduced into the YBC strain.

The ethanol-producing ability of the yeast is very strong. Particularly, yeast having a Crabtree effect consumes sugar while producing ethanol even in the presence of oxygen at a high sugar concentration. This strong ethanol-producing ability is due to the high activity of the enzyme and the action of a promoter that strongly expresses the enzyme. Therefore, in order to convert this ethanol-producing ability into lactate-producing ability, a strong promoter should be used along with a strong LDH enzyme. For this purpose, the present inventors conducted a study to increase the expression level using various known promoters of *Saccharomyces cerevisiae*, but failed to secure a promoter representing the desired expression level.

In general, promoters have various regulatory mechanisms and are thus often specialized for certain strains. Thus, in the present invention, the expression level of the gene associated with glycolysis and ethanol production in the target strain, the YBC strain (KCTC13508BP), was detected, and the g4423 gene was identified as the ADH gene that was most strongly expressed. It was considered that the ethanol production flux of the YBC strain could be replaced with the lactate production flux by replacing the identified ADH gene (g4423 gene) with an LDH gene having strong activity and then expressing the LDH gene through the g4423 promoter. In addition, the LDH gene introduced into the YBC strain should have strong activity of the enzyme produced therefrom, but the LDH gene should have excellent selectivity for pyruvate (i.e., the Km Value should be low) because it should compete with the PDC gene in the YBC strain for the substrate pyruvate. However, when measuring the Km value in vitro, it is preferable to determine the selectivity of LDH based on the results in vivo because the difference in Km value depending on the measurement conditions is great. Therefore, it is necessary to select an LDH gene that produces lactate well based on high activity and a low Km value. In order to reliably analyze (confirm) these characteristics, various known LDH genes were introduced directly into the site of the g4423 gene of the YBC strain, the lactate production ability was compared, and the optimal gene was selected.

In the present invention, the gene encoding lactate dehydrogenase is introduced so that expression of the gene is regulated by a promoter (SEQ ID NO: 3 or 4) of a g4434 gene.

In the present invention, the gene encoding the lactate dehydrogenase may be derived from *Lactobacillus plantarum*, and may be a gene encoding the amino acid sequence represented by SEQ ID NO: 1.

In the present invention, the recombinant strain may be characterized in that ethanol-producing ability is reduced compared to the parent strain, the YBC strain (KCTC13508BP), due to deletion or attenuation of the g4423 gene.

In one embodiment of the present invention, 57.1 g/L of lactate was produced in the recombinant strain of YBC introduced with the LDH derived from *Lactobacillus plantarum*, instead of the g4423 gene.

Accordingly, in another aspect, the present invention is directed to a method of producing lactic acid including (a) culturing the recombinant strain to produce lactic acid and (b) obtaining the produced lactic acid.

Through the present invention, it is possible to obtain an acid-resistant strain exhibiting greatly increased lactate production and greatly decreased ethanol production.

In another aspect, the present invention provides a gene construct including a promoter comprising the nucleotide sequence of SEQ ID NO: 3 or SEQ ID NO: 4 and a gene encoding lactate dehydrogenase operably linked to each other and a recombinant vector including the gene construct.

In the present invention, the gene construct may further include a terminator having the nucleotide sequence represented by SEQ ID NO: 5 or SEQ ID NO: 6.

In the present invention, the gene encoding the lactate dehydrogenase may be a gene encoding the amino acid sequence represented by SEQ ID NO: 1.

In another aspect, the present invention provides a method of producing lactic acid including (a) culturing the recombinant microorganism introduced with the gene construct or the recombinant vector, and (b) obtaining the produced lactic acid.

The g4423 promoter preferably has a sequence having a sequence homology of at least 90%, at least 92%, at least 93%, at least 95%, at least 97%, at least 98%, at least 99%, or 100%, with the sequence represented by SEQ ID NO: 3 or SEQ ID NO: 4.

In the case where a promoter has at least 90% homology with the g4423 promoter of the present invention and exhibits expression efficiency equivalent thereto, the promoter may be considered to be a substantially equivalent promoter.

In some cases, the g4423 promoter according to the present invention may be mutated through techniques known in the art in order to improve the expression efficiency of the target gene.

In the present invention, the recombinant yeast may have acid resistance, and it may be preferable to use a host yeast exhibiting resistance to organic acids in order to produce an acid-resistant recombinant yeast suitable for the present invention.

The acid-resistant yeast may be a yeast having acid resistance selected from the group consisting of the genus *Saccharomyces*, the species *Kazachstania saccharomyces* and the genus *Candida*, and is, for example, selected from the group consisting of *Saccharomyces cerevisiae*, *Kazachstania exigua*, *Kazachstania bulderi*, and *Candida humilis*, but is not limited thereto.

The term "acid-resistant yeast" means a yeast having resistance to organic acids such as 3-HP or lactic acid, and acid resistance can be determined by evaluating growth in a medium containing various concentrations of organic acids. That is, the term "acid-resistant yeast" means a yeast that exhibits a higher growth rate and biomass consumption rate than general yeast in a medium containing a high concentration of organic acid.

As used herein, the term "acid-resistant yeast" is defined as a yeast that can maintain a biomass consumption rate (such as a sugar consumption rate) of at least 10% or a specific growth rate of at least 10%, at a pH less than a pKa value of an organic acid when the medium contains an organic acid (particularly lactic acid) at a concentration of at least 1M, compared to when the medium does not contain an organic acid. More specifically, the term "acid-resistant yeast" is defined as yeast that can maintain a biomass consumption rate (such as a sugar consumption rate) of at least 10% or a specific growth rate of at least 10% at a pH of 2 to 4 compared to a pH of 7 or higher.

The recombinant yeast according to the present invention can be produced by inserting the gene into a chromosome of a host yeast according to a conventional method, or by introducing a vector including the gene into the host yeast.

As the host yeast, a host cell having high DNA introduction efficiency and high expression efficiency of the introduced DNA is commonly used. In one embodiment of the present invention, an acid-resistant yeast is used, but the present invention is not limited thereto and any type of yeast may be used as long as it can sufficiently express the target DNA.

The recombinant yeast can be prepared according to any transformation method. The term "transformation" refers to a phenomenon in which DNA is introduced into a host to enable DNA to be replicated as a factor of chromosomes or by chromosomal integration, and means a phenomenon in which genetic changes are artificially induced by introducing external DNA into a cell. General transformation methods include electroporation, lithium acetate-PEG, and the like.

In addition, in the present invention, any commonly known genetically engineering method can be used as a method of inserting genes into the chromosomes of host microorganisms. For example, there are methods using retroviral vectors, adenoviral vectors, adeno-associated virus vectors, herpes simplex viral vectors, pox viral vectors, lentiviral vectors, non-viral vectors and the like. The "vector" means a DNA product containing a DNA sequence operably linked to a suitable regulatory sequence capable of expressing the DNA in a suitable host. Vectors may be plasmids, phage particles or simply potential genomic inserts. When transformed into a suitable host, vectors may be replicated or perform functions independent of the host genomes, or some thereof may be integrated with the genomes. Plasmids are currently the most commonly used forms of vector, but linear DNA is also a commonly used form for genomic integration of yeast.

Typical plasmid vectors include (a) a replication origin to efficiently conduct replication so as to include a predetermined amount of plasmid vector in each host cell, (b) an antibiotic resistance gene or auxotrophic marker gene to screen host cells transformed with plasmid vectors, and (c) a restriction enzyme cleavage site into which a foreign DNA fragment is inserted. Even if an appropriate restriction enzyme cleavage site is not present, the vector and foreign DNA can be easily ligated using a synthetic oligonucleotide adapter or a linker according to a conventional method.

Furthermore, when a nucleic acid sequence is aligned with another nucleic acid sequence based on a functional relationship, it is "operably linked" thereto. This may be gene(s) and control sequence(s) linked in such a way so as to enable gene expression when a suitable molecule (e.g., a transcriptional activator protein) is linked to the control sequence(s). For example, DNA for a pre-sequence or secretory leader is operably linked to DNA for a polypeptide when expressed as a pre-protein involved in the secretion of the polypeptide; a promoter or enhancer is operably linked to a coding sequence when it affects the transcription of the sequence; or a ribosome-binding site is operably linked to a coding sequence when it affects the transcription of the sequence; or the ribosome-binding site is operably linked to a coding sequence when positioned to facilitate translation.

Generally, the term "operably linked" means that the linked DNA sequence is in contact therewith, or that a secretory leader is in contact therewith and is present in the reading frame. However, the enhancer need not be in contact therewith. The linkage of these sequences is carried out by ligation (linkage) at convenient restriction enzyme sites. When no such site exists, a synthetic oligonucleotide adapter or a linker according to a conventional method is used.

It should be understood that not all vectors function identically in expressing the DNA sequences of the present invention. Likewise, not all hosts function identically for the same expression system. However, those skilled in the art will be able to make appropriate selections from among a variety of vectors, expression control sequences and hosts without excessive burden of experimentation and without departing from the scope of the present invention. For example, selection of a vector should be carried out in consideration of a host because the vector should be replicated therein. The number of times the vector replicates, the ability to control the number of times the vector replicates, and the expression of other proteins encoded by the corresponding vector, such as the expression of antibiotic markers, should also be considered.

In the present invention, the carbon source may include, but is not limited to, one or more selected from the group consisting of glucose, xylose, arabinose, sucrose, fructose, cellulose, galactose, glucose oligomer, and glycerol.

In the present invention, the culture may be performed under conditions such that microorganisms, for example, *E. coli*, and the like no longer act (for example, cannot produce metabolites). For example, the culture may be carried out at a pH of 1.0 to 6.5, preferably a pH of 1.0 to 6.0, and more preferably a pH of 2.6 to 4.0, but is not limited thereto.

Hereinafter, the present invention will be described in more detail with reference to examples. However, it will be obvious to those skilled in the art that these examples are provided only for illustration of the present invention and should not be construed as limiting the scope of the present invention.

Example 1: Selection of Acid-Resistant Strain YBC and Effects Thereof

The present inventors selected a population of strains having acid resistance through testing on various yeast strains (Korean Patent Laid-open Publication No. 2017-0025315). The strain having the best acid resistance was determined by adding lactic acid to a medium at the beginning of the culture of yeast strains and monitoring the growth and sugar consumption rate of microorganisms. At this time, the OD of inoculation was 4, and the medium used herein was a YP medium (20 g/L peptone, 10 g/L yeast extract) supplemented with 3.5% of glucose, and the experiment was conducted in 50 ml of flask culture at 30° C. and 100 rpm, and culture was performed at an initial lactic acid concentration of 60 g/L. The YBC strain (*Kazachstania exigua* sB-018c) was selected as the strain having the best acid resistance by comparing and analyzing the results, and deposited under the terms of the Budapest Treaty with accession number KCTC13508BP at Biological Resource Center in the Korea Research Institute of Bioscience and Biotechnology as the depository authority, on Apr. 11, 2018 and accepted by the said depository authority. All restrictions on the availability to the public of the deposited material will be removed upon the granting of a patent for this application. The viability of the deposit will be maintained, for the duration of the patent term or for a period of twenty years, whichever is longer.

Phylogenetic analysis showed that the YBC strain is a strain similar to *S. cerevisiae*, is diploid and is Crabtree-positive.

In order to detect the acid resistance of the selected acid-resistant YBC strain, the strain was cultured under the same conditions as the *S. cerevisiae* (CEN.PK 113-7D) strain. 30 g/L and 60 g/L of lactic acid were each added to a YP medium supplemented with of 40 g/L of glucose, and then the OD values of the culture solutions were compared during incubation at 30° C. and 200 rpm for 50 hours. As shown in FIG. 1, for the YBC strain, it can be found that the YBC strain could grow even at a high lactic acid concentration of 60 g/L, whereas the *S. cerevisiae* CEN. PK strain could not grow at all at a lactic acid concentration of 60 g/L.

Example 2: Identification of Main Expressed Gene by Detection of Expression Rate of Alcohol-Producing Gene in YBC Strain In this example, the ADH gene was targeted in order to select a gene that is highly effective without affecting growth during strongly expression and replacement with the gene from among genes associated with glycolysis and ethanol production that are strongly expressed in the presence of glucose in the YBC strain. In particular, genes associated with glycolysis should be avoided in order not to directly affect microbial growth. The reason for this is that, when the genes associated with glycolysis are lost or reduced, the production of pyruvate, which is important for microbial growth, is inhibited or a problem in the balance of the chain reaction occurs, thus affecting microbial growth and consequently deteriorating the fermentation ability. Therefore, when the target strain is an ethanol-producing strain, the PDC gene or the ADH gene is selected as an intrinsic gene for gene replacement, and ADH is selected and removed in consideration of the negative effect of PDC knockout (K/O).

Strains with strong ethanol fermentation ability, such as yeast, contain ADHs that have a wide variety of strengths and functions, and the main ADH functioning to produce ethanol is identified among ADHs of the YBC strain, and several candidate genes were selected by comparing the genome information of YBC and the known ADH gene information of *S. cerevisiae* in order to use the corresponding promoter, and qPCR was performed thereon.

Seven ADH gene candidates present in the genome of the YBC strain were selected using bioinformatics information in the full genome sequence data of *S. cerevisiae*, and RT-qPCR was performed by designing oligomers specific for the selected genes.

Seven ADH gene candidates were selected using bioinformatics information in the genome-wide sequence data of *S. cerevisiae* (Table 1), and RT-qPCR was performed by designing oligomers specific for the selected genes (Table 2).

TABLE 1

| *S. cerevisiae* gene | Homolog in YBC | Identity-% (protein) | Genomic location* | Targeting signal |
|---|---|---|---|---|
| ADH1 | g4423 | 89.1% | ADH5 | no |
| ADH2 | g4423 | 77.2% | ADH5 | no |
| ADH3 | g2289 | 80.4% | ADH3 | mitochondrial |
| ADH4 | No homologs | | | |
| ADH5 | g4423 | 74.4% | ADH5 | no |
| SFA1 | g4117 | 79.5% | SFA1 | |
| ADH6 | g5126 | 63.4% | — | no |
| | g1044 | 64.1% | — | no |
| | g4395 | 64.0% | — | no |
| | g727 | 63.7% | — | no |
| | g2807 | 60.4% | — | no |
| ADH7 | g5126 | 63.0% | — | no |
| | g1044 | 60.0% | — | no |
| | g4395 | 61.8% | — | no |
| | g727 | 62.1% | — | no |
| | g2807 | 58.0% | — | no |

*Genes having similar gene sequence in YBC compared to *S. cerevisiae* genome

TABLE 2

Primers for qPCR

| Name | SEQ ID NO | Sequence | Description |
|---|---|---|---|
| oSK-1318 | 11 | CGGACTTTAGAGCCTTGTAGAC | g4423 qPCR fwd |
| oSK-1319 | 12 | ATCTGGTTACACTCACGATGG | g4423 qPCR rev |
| oSK-1320 | 13 | CCAAGTACGTTAGAGCTAACGG | g4423 qPCR 2 fwd |
| oSK-1321 | 14 | GAGCTTCTCTGGTATCAGCT | g4423 qPCR 2 rev |
| oSK-1322 | 15 | AGCTTTAGCAAACATTAGACCC | g1044 qPCR fwd |
| oSK-1323 | 16 | ATTCCATCCGAATATGCTGGT | g1044 qPCR rev |
| oSK-1324 | 17 | GGAACCTAAATGACTGTTGGCA | g1044 qPCR 2 fwd |
| oSK-1325 | 18 | AGGATGTTGATTTCGACTCGT | g1044 qPCR 2 rev |
| oSK-1326 | 19 | TTCCAAAGGGTACCAATTTAGCTG | g2289 qPCR fwd |
| oSK-1327 | 20 | GTACCGCTAATGAACCTAAACCA | g2289 qPCR rev |
| oSK-1328 | 21 | AGAGCTGACACTAGAGAAGCC | g2289 qPCR 2 fwd |
| oSK-1329 | 22 | GATGTGTCTACGACGTATCTACC | g2289 qPCR 2 rev |
| oSK-1330 | 23 | GTACTGGTAACGTCCAAGTC | g4117 qPCR fwd |
| oSK-1331 | 24 | GAACCCTTCCATACTCTACCA | g4117 qPCR rev |
| oSK-1332 | 25 | TTCAGTTCGTGCTACTCAAGG | g4117 qPCR 2 fwd |
| oSK-1333 | 26 | TCAATTGCAACGACAGAGAC | g4117 qPCR 2 rev |
| oSK-1334 | 27 | CCGTACCCTGAAGAGTTTACTG | g2807 qPCR fwd |
| oSK-1335 | 28 | CAACCATAGATTCACGAATTGCTC | g2807 qPCR rev |
| oSK-1336 | 29 | AGTGGATTTGGATTAATGGGTG | g2807 qPCR 2 fwd |
| oSK-1337 | 30 | GCTTCTGTAACACCTTTAACAC | g2807 qPCR 2 rev |
| oSK-1338 | 31 | AAATTGGTGACCGTGTTGGT | g727 qPCR fwd |
| oSK-1339 | 32 | AACCACCTTTACTACGGTAACCA | g727 qPCR rev |
| oSK-1340 | 33 | TTTAGTCGTCATCTGTTCAGGT | g727 qPCR 2 fwd |
| oSK-1341 | 34 | GAGACACCTAACAAACCAAATGG | g727 qPCR 2 rev |
| oSK-1342 | 35 | GATTCAAGCTTCTTCTCGTATCGG | g3610 qPCR fwd (ALG9 homolog) |
| oSK-1343 | 36 | GGAAATGATACCATTCACGACCT | g3610 qPCR rev (ALG9 homolog) |
| oSK-1350 | 37 | GTTCCGTCAAAGAAATCAAGCA | g5126 qPCR fwd |
| oSK-1351 | 38 | TGGTAAACCTGTATCTGACATCAC | g5126 qPCR rev |
| oSK-1352 | 39 | TTTAGTTGTCATTTGTGCCGGT | g5126 qPCR 2 fwd |
| oSK-1353 | 40 | GACACCTAACAAACCAAACGGA | g5126 qPCR rev |
| oSK-1386 | 41 | CTTTGAGTGCAAGTATCGCC | ALG9 qPCR fwd |
| oSK-1387 | 42 | TGTGTAATTGTTCACCAAAGCC | ALG9 qPCRrev |

Figure 2:
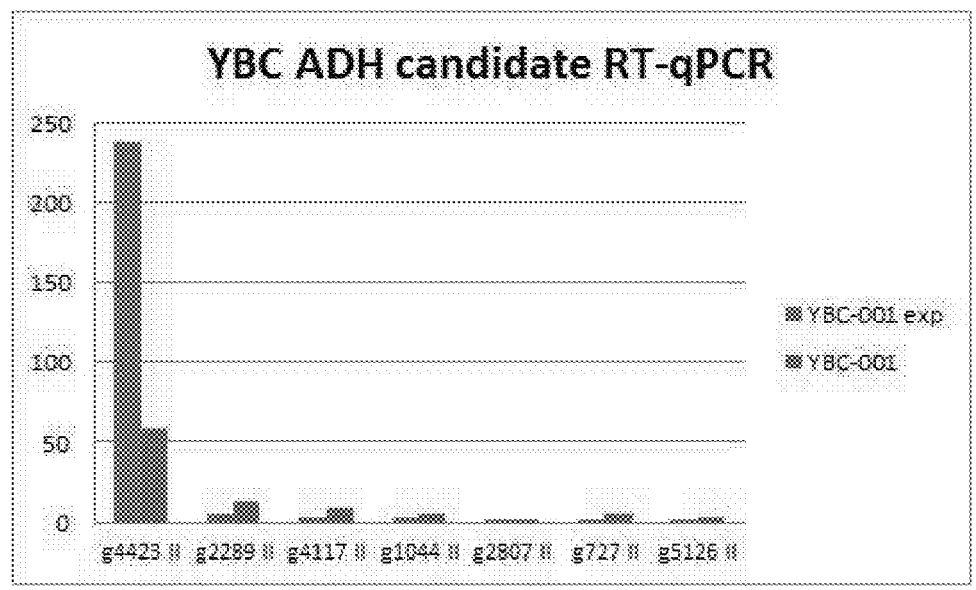
FIG. 2 shows the result of confirming the expression level of the ADH candidate gene in the YBC strain.

As a result, as shown in FIG. 2, the expression level of the g4423 gene was found to be remarkably high, so g4423 was identified as the main ethanol-producing gene.

Example 3: Detection of Effect of Reducing Ethanol Production when Removing g4423 from YBC Strain A recombinant strain was produced by knocking out g4423, which is the main ADH of the YBC strain identified in Example 2, and the effect of ADH removal on the growth of the strain was detected.

Figure 4:
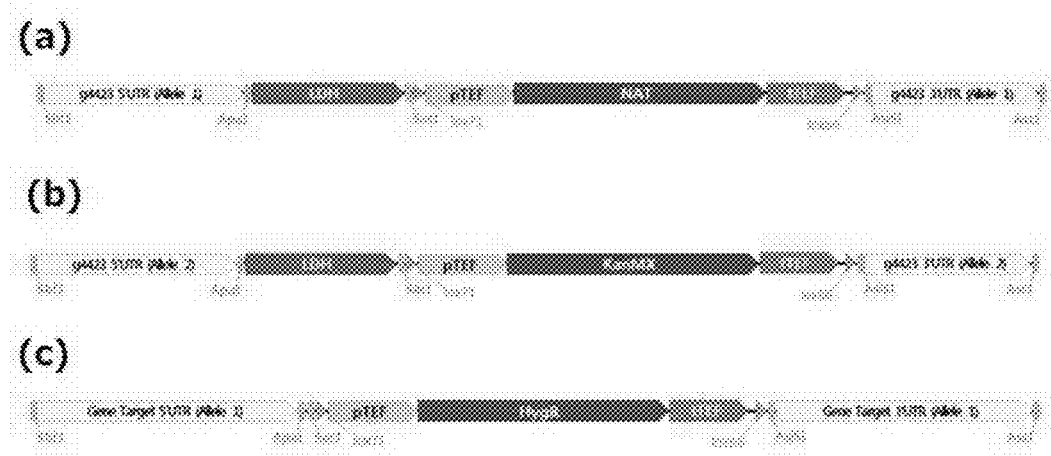
FIG. 4 shows examples of gene cassettes for expressing LDH in each allele or removing a target gene, wherein (a) is a cassette that expresses LDH in allele1 of g4423, (b) is a cassette that expresses LDH in allele2 of g4423, and (c) is an example of a cassette for removing a target gene.

A gene cassette similar to FIG. 4(c), which had 5' and 3' UTR and antibiotic markers and from which the g4423 ORF was removed, was produced based on the information of g4423 and UTR, and was used as donor DNA. The donor DNA was produced using a cloning method using a restriction enzyme and a method using Gibson assembly as described above. Removal of the ORF was detected using primers for ORF (Primer forward (SEQ ID NO: 43): GAGATAGCACACCATTCACCA, Primer reverse (SEQ ID NO: 44): CAACGTTAAGTACTCTGGTGTTTG) to identify g4423 in colonies grown on a plate corresponding to the marker gene after introducing the prepared donor DNA.

The produced g4423 knockout strain was cultured in 150 ml in YP medium having a glucose concentration of 40 g/L at 30° C. and 200 rpm.

Figure 3:
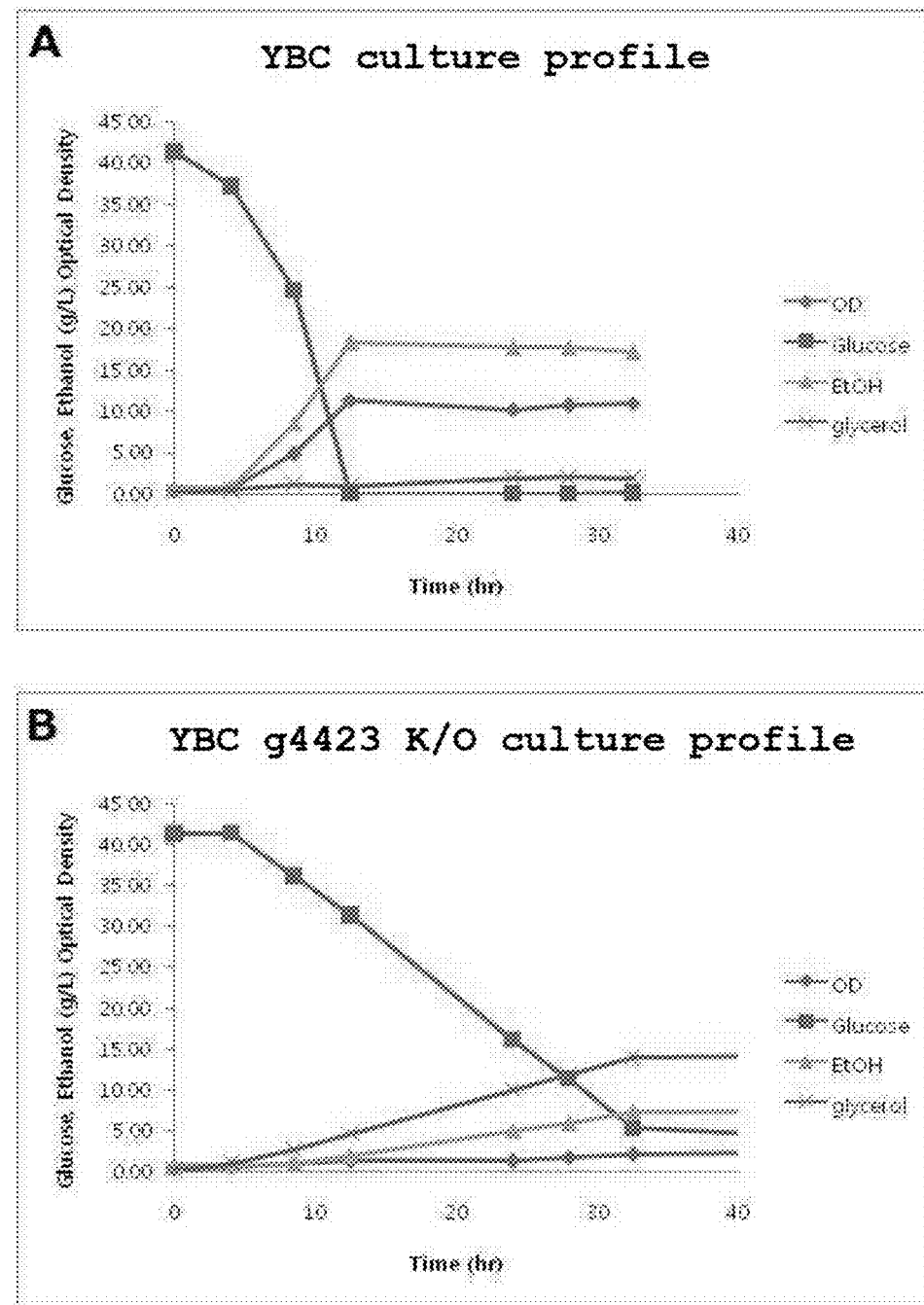
FIG. 3 shows the result of confirming the ethanol-producing ability of a wild-type YBC strain and a G4423 knockout strain.

As a result, as can be seen from FIG. 3, the g4423 knockout strain (FIG. 3B) exhibited significantly reduced ethanol-producing ability compared to the wild-type YBC strain (FIG. 3A), had lowered glucose uptake ability due to the reduced ADH activity and thus limited NADH oxidation, and thus exhibited deteriorated growth and increased glycerol production to compensate this.

Example 4: Expression of Known LDH Gene and Selection of Optimal LDH Using g4423 Promoter Candidate genes for LDH genes to be introduced into the YBC strain were selected based on the literature (N. Ishida et. al., Appl. Environ. Microbiol., 1964-1970, 2005; M. Sauer et al., Biotechnology and Genetic Engineering Reviews, 27:1, 229-256, 2010), and three genes in total, namely, *L. helveticus*-derived LDH gene, *R. oryzae*-derived LDH gene, and *L. plantarum*-derived LDH gene, were selected.

As the gene of each enzyme, LDH, which is expressed at a high level in yeast and produces lactate well, was selected based on the above literature and the enzyme having no or little difference in performance between acidic conditions where pH<pKa and a general pH higher than pH>pKa was selected. In addition, a gene requiring no fructose-1,6-diphosphate was selected as a coenzyme other than NADH. The Km value of the corresponding gene could be compared in many literatures and one capable of producing a great amount of flux due to the relatively low Km value when competing with the PDC enzyme inside the YBC was selected. However, the Km value, when measured in vitro, changes depending on factors such as media, substrate concentration and coenzyme concentration, so the actual performance should be evaluated directly based on the result of fermentation in each strain.

Therefore, each of the selected three genes was introduced into the YBC strain to produce recombinant strains using the g4423 promoter, and the ability of each recombinant strains to produce lactic acid was determined.

The gene cassette of FIG. 4(a), from which the g4423 ORF was removed and in which 5' and 3' UTR and antibiotic markers were present, was produced based on the information of g4423 and UTR, and LDH of *Lactobacillus plantarum*, *Lactobacillus helveticus* and *Rhizopus oryzae* was synthesized with sequences optimized respectively through yeast codon usage for 3 types of LDH (gene sequences of SEQ ID NOs: 2, 8, and 10 and amino acid sequences of SEQ ID NOs: 1, 7 and 9), and then introduced into the ORF site of g4423 using a restriction enzyme.

The donor DNA was amplified in the completed cassette and transformed into the YBC strain, and the presence of primers to identify the g4423 ORF (primer forward ORF inside (SEQ ID NO: 45): CAACGTTAAGTACTCTGGTGTTTG, primer reverse ORF inside (SEQ ID NO: 46): GAGATAGCACACCATTCACCA, primer forward ORF outside (SEQ ID NO: 47): 5' GGATTCCTGTAATGACAACGCGAG, and primer reverse ORF outside (SEQ ID NO: 48): 3' TGGATACATTACAGATTCTCTATCCT) and the ORF of each LDH in grown colonies was identified, so it was found that each LDH was introduced in 1 copy using the following primers:

*L. helveticus* Primer forward (SEQ ID NO: 49): ATGAAAATTTTTGCTTATGG

*L. helveticus* Primer reverse (SEQ ID NO: 50): TTAATATTCAACAGCAATAG;

*R. oryzae* Primer forward (SEQ ID NO: 51): ATGGTTTTGCATTCTAAAGT

*R. oryzae* Primer reverse (SEQ ID NO: 52): TTAACAAGAAGATTTAGAAA

*L. plantarum* Primer forward (SEQ ID NO: 53): ATGTCTTCTATGCCAAATCA

*L. plantarum* Primer reverse (SEQ ID NO: 54): TTATTTATTTTCCAATTCAG

Since the YBC strain is a diploid strain, even when one LDH gene is inserted into the strain, another g4423 gene acts, and thus the amount of ethanol that is produced is not reduced as much as that of the completely knocked out (K/O) strain.

The produced recombinant strain was shake-cultured in a flask at 30° C./100 rpm for 24 hours using a YP medium supplemented with 4% glucose and 150 mg/L of uracil.

Lactate and ethanol in the culture solution were observed through HPLC. The concentration of glucose, ethanol and L-lactate in the culture solution was analyzed using a Bio-Rad Aminex 87-H column mounted on a Waters 1525 Binary HPLC pump. Glucose and ethanol were analyzed using a Waters 2414 refractive index detector, L-lactate was analyzed using a Waters 2489 UV/Visible detector (210 nm), the peak area standard curve depending on the concentration for each component was drawn, the concentration was calculated, and the specific analysis conditions are as follows.

1. Mobile Phase Condition: 0.005M $H_2SO_4$ solution
2. Flow rate: 0.6 mL/min
3. Run time: 40 min
4. Column Oven temperature: 60° C.
5. Detector temperature: 40° C.
6. Injection volume: 10 μL
7. Auto sampler tray temperature: 4° C.

Figure 5:
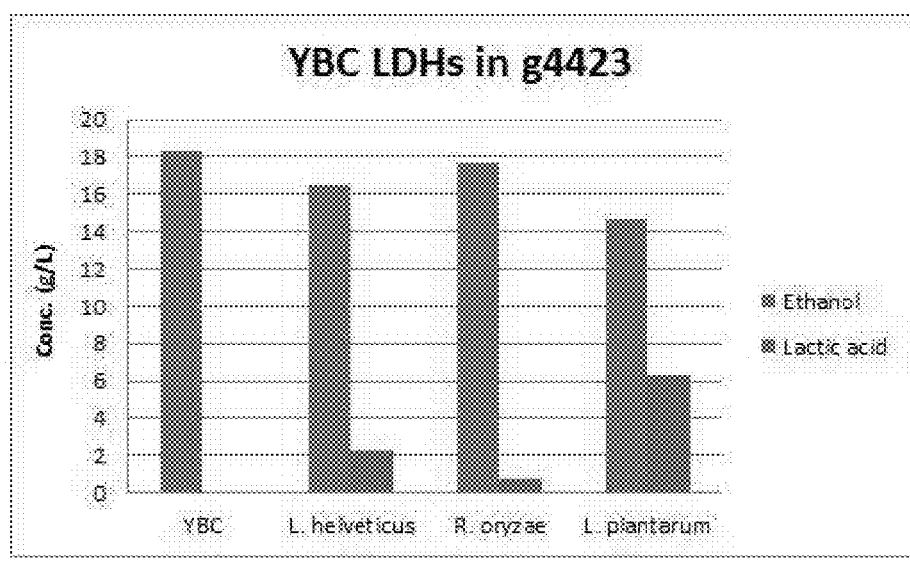
FIG. 5 shows the result of confirming the lactic acid production ability of the YBC recombinant strain introduced with LDH derived from three strains.

As a result, as can be seen from FIG. 5 and Table 3, all of the substituted target genes exhibited LDH activity, and the strain into which the LDH gene derived from *L. plantarum* was introduced exhibited the highest lactic acid production ability.

Table 3 shows the Km values reported in the literature of the corresponding LDH. However, this number can be used only for comparison between tested enzymes under the same conditions, and is not meant to be a fixed value. In this experiment, it was also found that LDH expressed from a gene derived from *L. plantarum* having a relatively high Km value was able to compete with the PDC gene in the strain and to produce lactate well. In addition, the above results showed that the gene that competes with PDC in the acid-resistant strain YBC and exhibits the highest lactic acid production ability is the LDH gene derived from *L. plantarum*.

TABLE 3

|  | L-LDH | | |
| --- | --- | --- | --- |
|  | L. helveticus | R. oryzae | L. plantarum |
| Km value of enzyme | 0.25 ① | 1.3~4.8 ② | 4.3 ③ |
| Lactate (g/L) | 2.3 | 0.8 | 6.0 |

① Kirsi savijoki and Airi Palva, *Applied and Environmental Microbiology*, 2850-2856, 1997
② Christopher D. S. et al., *Enzyme and Microbial Technology* 44(2009) 242-247, 2009
③ Anna Feldman-Salit et al., *The Journal of Biological Chemistry*, 288, 21295-21306. 2013

Example 5: Confirmation of Blocked Ethanol Production and Lactate Production Ability Using Selected LDH A recombinant strain, in which 2 copies of the LDH gene derived from *L. plantarum* selected in Example 4 were introduced in place of the g4423 gene of the YBC strain, was produced, and the ability thereof to produce lactic acid was determined.

The corresponding YBC strain has a diploid genome. The present inventors created the donor DNA having different antibiotic resistance genes for each allele as shown in FIGS. 4(a) and (b) by the production method of Example 4 and then introduced the donor DNA into the YBC strain for each allele twice. Then, complete removal of g4423 ORF was identified using the ORF primer of g4423, and the presence of each antibiotic resistance gene indicated that 2 copies of the gene were introduced. The presence of an antibiotic resistance gene disables genetic manipulation in the future, so each antibiotic resistance gene was removed using the Cre-LoxP method introduced in the cassette.

The ability to produce lactic acid was determined in a fermentor using the recombinant strain. The medium used herein was a Hestrin and Schramm medium (glucose 120 g/L, peptone 5 g/L, yeast extract 5 g/L, citric acid 1.15 g/L, $K_2HPO_4$ 2.7 g/L, $MgSO_4 \cdot 7H_2O$ 1 g/L), and was cultured at a sugar concentration of 120 g/L in a fermentor having a volume of 1 L. The culture temperature was 30° C., the pH was adjusted to 3, and a stirring rate was maintained at 350 to 450 rpm.

Figure 6:
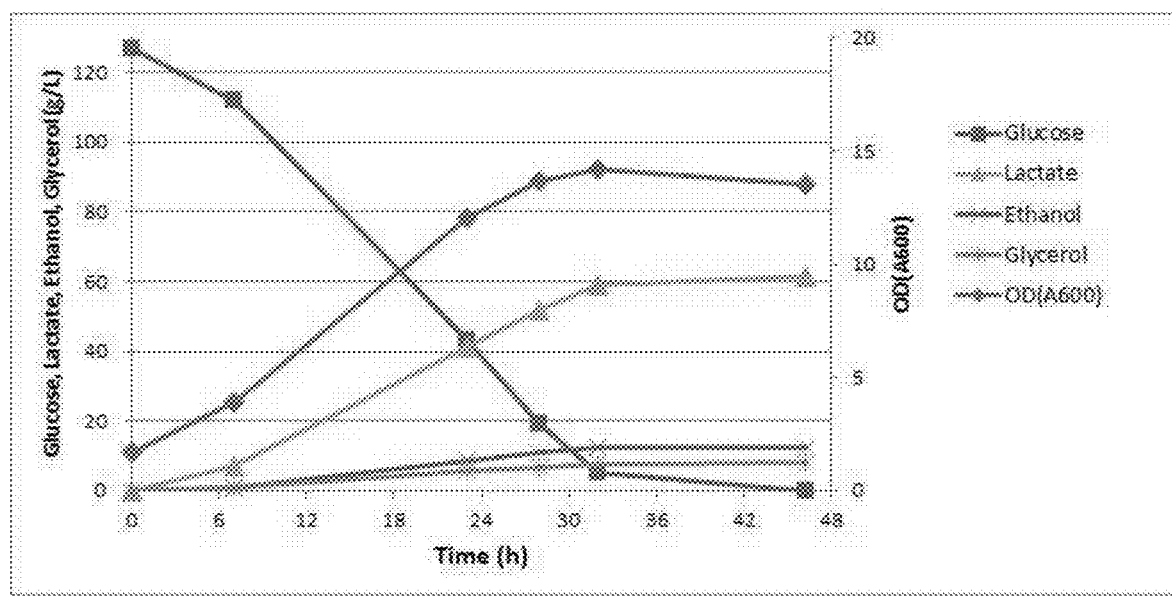
FIG. 6 shows the result of confirming the lactic acid production ability of a recombinant strain in which 2 copies of the LDH gene were introduced at the location of the g4423 gene of the YBC strain.

As a result, as can be seen from FIG. 6, growth inhibition by acetaldehyde, which is generally observed in the strain from which ADH was removed, was not detected, and there was no increase in glycerol production, which indicates that the oxidation of NADH occurs well and the internal redox balance is well balanced due to the newly expressed LDH enzyme. In addition, when additional LDH is expressed, the oxidation rate of NADH is further accelerated, and the productivity and concentration of lactate can be further increased.

The above results represent a great improvement over the results using previously known ADH blocking and related LDH expression (Kenro Tokuhiro et al., *Applied Microbiology and Biotechnology*, 82:883-890, 2009). First, it can be seen that sugar is readily consumed and converted to lactate, even though the production of ethanol is greatly reduced. The low level of glycerol means that the oxidation reaction of NADH is faithfully performed by strongly expressed LDH. It can be seen from the OD value of the culture solution that the acid resistance of lactic acid was maintained and the toxic effect of acetaldehyde, an intermediate product of ethanol blocking, was very small. These performance indicators also show that, when performing conversion to lactate by blocking the production of ethanol, the three indicators, namely yield, concentration and fermentation rate, increase smoothly and achieve the goal of developing commercially applicable strains.

A more detailed description will be given using the conventional technology as an example. When ADH is blocked as described above, ethanol production may decrease, but pyruvate and acetaldehyde, the precursor of ethanol, accumulate in proportion to the decrease, resulting in increased toxicity to cells. In addition, blocking ADH inhibits the oxidation reaction of NADH that occurs through ADH, greatly reduces the sugar consumption rate, and increases the production of glycerol, another reducing material, in order to solve this, resulting in decreased productivity of lactic acid and increased productivity of byproducts. In this case, when LDH is effectively expressed, this phenomenon is reduced due to NADH oxidation by LDH. However, since the Km value of LDH competes with the PDC enzyme in the cell, a sufficient amount of the enzyme should be strongly expressed while lactate could be smoothly produced, in order to oxidize NADH while preventing a decrease in sugar consumption rate and growth inhibition, and solving problems caused by ADH blockage. With conventional technologies, it was difficult to solve these problems and it was difficult to completely solve the problem of a decreased sugar consumption rate in spite of attempts to alleviate the problems by operating the TCA cycle through strong aeration to promote the oxidation of NADH.

Related examples are shown in Tables 4 and 5 below.

It can be seen that, when LDH is expressed in a strain in which main ADH is blocked (Adh1(pLdhA68X)), the yield, productivity and concentration are notably low, which means that it is difficult to produce lactate through ADH blocking when strong expression of LDH and selection of appropriate LDH are not realized from the related art. In addition, it is further difficult to realize such a technique in acid-resistant strains so as to smoothly produce lactic acid at a low pH.

It can be seen that, when LDH is expressed using an ADH1 promoter in a strain with no ADH blocking as a comparative group, lactate production and strain growth are performed well due to LDH (the amount of ethanol produced is decreased due to competitive reaction between LDH and PDC) and the negative effects described above occur due to blocking ADH. However, obviously, further improvement of yield is impossible in strains not capable of blocking ethanol production due to the competition in yield of lactate and ethanol from pyruvate.

In addition, for reference, one study describes that LDH is responsible for the oxidation of NADH and produces lactic acid by expressing LDH in a strain in which PDC activity remained at a level of 2% compared to the wild-type strain. The strain (YSH 4.123.-1C(pLdhA68X)) retained 2% of PDC activity compared to the wild type for the supply of cytoplasmic acetyl-CoA as described above. As a result, it was found that ethanol was produced at 10 g/L, and this value corresponds to a yield loss of 10/92×90.08/46.07=0.21 based on lactic acid production, which means that, with PDC activity control using knockdown in this way, it is difficult to block ethanol production during lactic acid production. In addition, it is well known that, when completely removing PDC activity, cell growth is seriously inhibited due to the restriction of supply of cytosolic acetyl coA, as reported in the literature.

TABLE 4

Strains and Plasmids

| Strain | Description |
|---|---|
| YBC-001 | YBC wt |
| YBC-Ldh1 | YBC Δg4423::ldh |
| InvSc1 | *Saccharomyces cerevisiae*, Diploid, Matα, his3Δ1, leu2, trp1-289, ura3-52 (Invitrogen Corp) - Adh is intact |
| Adh1 | *Saccharomyces cerevisiae*, Haploid, Matα, can1-100, ade2-1, lys2-1, ura3-52, leu2-3/112, trp1- Δ901, adh1-0 (Institut fur Mikrobiologie, Frankfurt am Main) |
| YSH 4.123.-1C | *Saccharomyces cerevisiae*, Haploid, Matα, leu2-3/112, trp1 -92, tra3-52, pdc1-14 (Gφteborg University): PDC activity 2% remained |
| pLdhA68X | Plasmid containing *R. oryzae* LDH in *S. cerevisiae* Adh1 promoter |

TABLE 5

Lactic acid production ability of strains

| | Lactic acid (g/L) | Yield (g/g) | Production efficiency (g/L/hr) | Reference |
|---|---|---|---|---|
| InvSc1(pLdhA68X) | 38.0 | 0.445 | 1.2 | Christopher D. Skory, *J. Ind. Microbiol. Biotechnol.* (2003) 30: 22-27: yield in lactic acid further decreases under the condition of pH > pKa, at a lower pH. |

TABLE 5-continued

Lactic acid production ability of strains

| | Lactic acid (g/L) | Yield (g/g) | Production efficiency (g/L/hr) | Reference |
|---|---|---|---|---|
| Adh1(pLdhA68X) | 17.0 | 0.17 | 0.25 | the same as above |
| YSH 4.123.-1C(pLdhA68X) | 31.0 | 0.336 | 0.72 | the same as above |
| YBC-LDH1 | 57.1 | 0.53 | 1.78 | Present invention |

Through the present invention, an excellent acid-resistant strain exhibiting greatly increased lactate production and greatly decreased ethanol production was obtained.

In order to confirm the acid resistance of the recombinant strain of the present invention, fermentation was performed by adjusting the pH upon fermentation with NaOH as a base to pH 4 and pH 5, which is greater than or equal to the pKa value of lactic acid.

Figure 7:
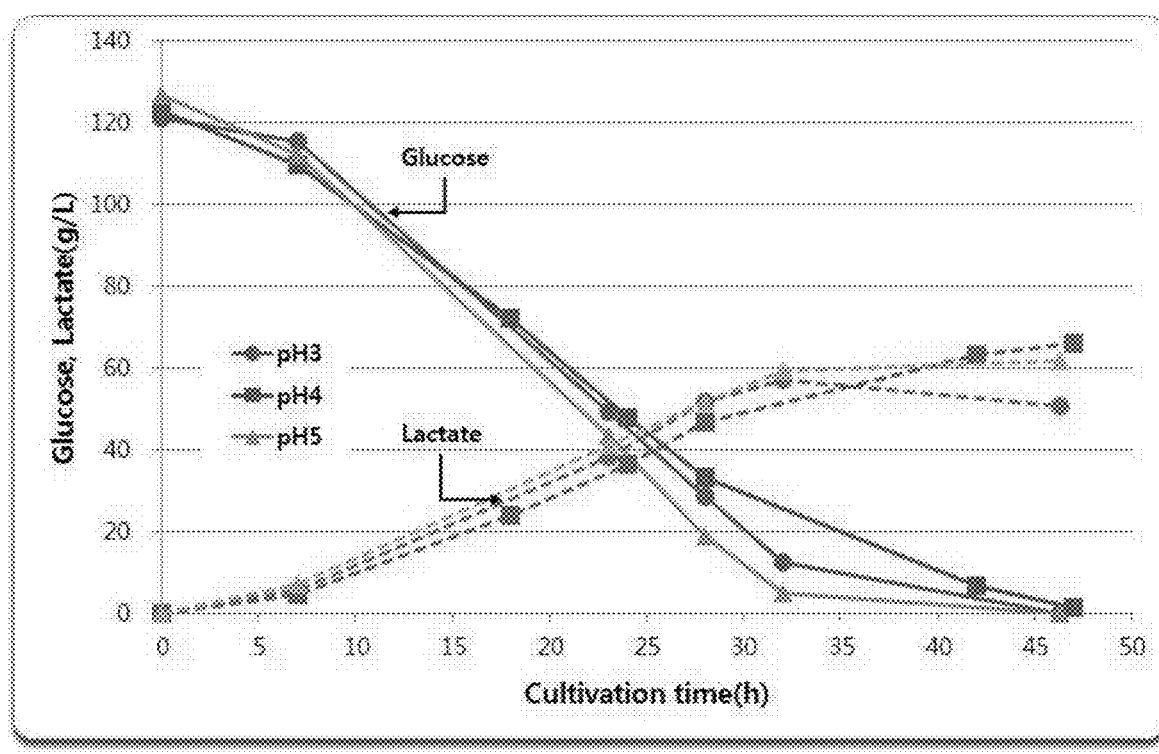
FIG. 7 shows the result of comparing the lactic acid production ability at different pHs of the recombinant strain in which 2 copies of the LDH gene was introduced at the location of the g4423 gene of the YBC strain.

As a result, as can be seen from FIG. 7, the performance of the strain even at a pH lower than pKa was similar to the performance at a high pH, which shows that there is no deterioration in the performance at a pH below pKa, which is observed in conventional lactic-acid-producing strains using yeast, and sufficiently supports that the corresponding strain has acid resistance. In addition, the recombinant strain of the present invention exhibited performance of consuming all of the sugar of 120 g/L at pH 3, pH 4 and pH 5, which can also be considered to be a result sufficiently showing the acid resistance of the strain. Table 6 shows an example of the performance degradation depending on the pH that occurs in the development of lactic-acid-producing strains using a general yeast.

TABLE 6

Performance depending on pH of lactic-acid-producing strains using general yeast

| Yeast | LDH | pH < pKa performance | pH > pKa performance | Reference |
|---|---|---|---|---|
| *S. cerevisiae* | *B. taurus* (multicopy plasmid) | 6.1 g/L Lactic acid, 0.23 g/L/hr productivity | 11.4 g/L Lactic acid, 0.3 g/L/hr productivity | Michael Sauer et al., *Biotechnology and Genetic Engineering Reviews*, 27: 229-256, 2010 |
| *K. marxianus* | *L. helveticus* (integrated into PDC1 locus) | 9.1 g/L Lactic acid, 0.13 g/L/hr productivity | 99 g/L Lactic acid, 2 g/L/hr productivity | The same as above |
| *P. stipitis* | *L. helveticus* (integrated, 1 copy) | 15 g/L Lactic acid, 0.17 g/L/hr productivity | 58 g/L Lactic acid, 0.39 g/L/hr productivity | The same as above |
| *S. cerevisiae* | *L. mesenteroides* | 48.9 g/L Lactic acid, 0.41 g/L/hr productivity | 112 g/L Lactic acid, 2.2 g/L/hr productivity | Seung Ho Baek, et al., *Appl Microbiol Biotechnol*, 2016 Mar; 100(6): 2737-48. |

Depositary Information
Name of Depositary Authority: Korea Research Institute of Bioscience and Biotechnology
Accession number: KCTC13508BP
Deposit Date: 20180411

INDUSTRIAL APPLICABILITY

The acid-resistant yeast according to the present invention can effectively inhibit the production of ethanol, express LDH enzyme at a high level and high efficiency, and produce lactic acid in high yield without growth deterioration even at a low pH.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

Sequence Listing Free Text

An electronic file is attached.

The invention claimed is:

1. A recombinant strain having lactic-acid-producing ability, in which a g4423 gene encoding ADH (alcohol dehydrogenase) is deleted or attenuated from YBC strain (KCTC13508BP) and a gene encoding a lactate dehydrogenase (LDH) encoding the amino acid sequence of SEQ ID NO: 1 is introduced into the YBC strain (KCTC13508BP) so that expression of the gene encoding LDH is regulated by a promoter comprising the nucleotide sequence of SEQ ID NO: 3 or SEQ ID NO: 4.

2. The recombinant strain according to claim 1, wherein the recombinant strain has a reduced ethanol-producing ability compared to that of YBC strain (KCTC13508BP), as a parent strain, by deletion or attenuation of the g4423 gene.

3. A method of producing lactic acid comprising:
   (a) culturing the recombinant strain according to any one of claim 1 to produce lactic acid; and
   (b) obtaining the produced lactic acid.

* * * * *